United States Patent
Kim

(10) Patent No.: US 7,256,884 B2
(45) Date of Patent: Aug. 14, 2007

(54) PARTICLE DETECTING SYSTEM AND METHOD OF DETECTING PARTICLES USING THE SAME

(75) Inventor: Sang-Hun Kim, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 144 days.

(21) Appl. No.: 11/138,680

(22) Filed: May 27, 2005

(65) Prior Publication Data

US 2005/0264799 A1 Dec. 1, 2005

(30) Foreign Application Priority Data

May 28, 2004 (KR) ...................... 10-2004-0038060

(51) Int. Cl.
*G01N 21/00* (2006.01)

(52) U.S. Cl. .................................. 356/239.8

(58) Field of Classification Search ................ 356/237, 356/239, 239.8; 359/228, 229, 665, 666; 250/216
See application file for complete search history.

(56) References Cited

U.S. PATENT DOCUMENTS

| | | | |
|---|---|---|---|
| 4,966,457 A * | 10/1990 | Hayano et al. ........... 356/239.7 |
| 4,999,510 A * | 3/1991 | Hayano et al. ......... 250/559.41 |
| 5,072,128 A * | 12/1991 | Hayano et al. ......... 250/559.18 |
| 5,363,187 A * | 11/1994 | Hagiwara et al. ........ 356/237.3 |
| 5,381,225 A * | 1/1995 | Kohno .................... 356/237.5 |
| 5,410,400 A * | 4/1995 | Shishido et al. ......... 356/237.4 |
| 5,436,464 A * | 7/1995 | Hayano et al. ......... 250/559.01 |
| 5,539,514 A * | 7/1996 | Shishido et al. ......... 356/237.4 |
| 5,563,702 A * | 10/1996 | Emery et al. .................. 356/73 |
| 5,574,598 A * | 11/1996 | Koumura et al. ........... 359/666 |
| 5,862,054 A | 1/1999 | Li |
| 6,369,954 B1* | 4/2002 | Berge et al. ................. 359/666 |
| 6,459,491 B1* | 10/2002 | Nguyen ...................... 356/604 |
| 6,545,815 B2 | 4/2003 | Kroupenkine et al. |
| 6,545,816 B1* | 4/2003 | Kroupenkine et al. ...... 359/665 |
| 6,636,301 B1* | 10/2003 | Kvamme et al. ......... 356/237.2 |
| 7,046,447 B2* | 5/2006 | Raber .......................... 359/625 |
| 2001/0017985 A1* | 8/2001 | Tsuboi et al. ................ 396/506 |
| 2003/0011786 A1* | 1/2003 | Levy et al. .................. 356/600 |
| 2003/0060916 A1 | 3/2003 | Hsieh |
| 2004/0227063 A1* | 11/2004 | Viinikanoja ................. 250/216 |
| 2006/0262433 A1* | 11/2006 | Hendriks et al. ........... 359/846 |

OTHER PUBLICATIONS

Berge et al., "Variable focal lens controlled by an external voltage: An application of electrowetting", Eur. Phys. J. E 3, 159-163 (2000).*
Krupenkin et al., "Tunable liquid microlens", Applied Physics Letters, vol. 82, No. 3, pp. 316-318, (Jan. 20, 2003).*

* cited by examiner

*Primary Examiner*—Tarifur Chowdhury
*Assistant Examiner*—Daniel Cartoon
(74) *Attorney, Agent, or Firm*—Volentine & Whitt, PLLC

(57) ABSTRACT

There is provided a particle detector system and to detect particles on target including reticle and pellicle. The system includes a light transmitting device adapted to transmit light beam to a target through an electrowetting microlens, a light receiving device adapted to receive the transmitted light beam reflected by a surface of the target, a light refraction angle adjusting controller adapted to apply a voltage to the electrowetting microlens in order to adjust an incident angle of the light irradiated, and a detector adapted to analyze the light received by the light receiving device to determine whether there are particles on a surface of the target.

13 Claims, 5 Drawing Sheets

PARTICLE DETECTING SYSTEM AND METHOD OF DETECTING PARTICLES USING THE SAME

BACKGROUND OF THE INVENTION

1. Technical Field

The present invention generally relates to a particle detector and a method of using the same. More particularly, the present invention generally relates to a system used to detect particles by using an electrowetting microlens and a method of detecting particles using the same.

A claim of priority is made to Korean Patent Application No. 2004-0038060, filed May 28, 2004, the disclosure of which is hereby incorporated herein by reference in its entirety.

2. Discussion of Related Art

Developments in semiconductor devices are increasing almost on a daily basis. The development of ultra highly integrated semiconductor devices has advanced the electronic communication industry and the multimedia field. The development of the semiconductor devices is an aggregate of circuit design technology, equipment technology, and process technology.

Manufacturing processes for a semiconductor device consist of photo-lithography, etching, ion implantation, thin film formation, and metal wiring. Among these processes, a pattern formation by a photo-lithography process is a key process in the manufacture of the ultra highly integrated semiconductor devices. The photo-lithography process is divided into a coating step, an exposure step, and a development step. The exposure step and equipment used for the exposure step are very important in the photo-lithography process.

During the exposure step, a substrate is coated with a photo-resist, a soft bake is performed on the substrate, and a temporary phase is formed on the photo-resist.

To perform the exposure step, an exposure device capable of transferring a circuit pattern onto a substrate is used. Recently, a projection exposure device has been used to transfer a photo-mask pattern or reticle onto a substrate such as a semiconductor substrate or a glass plate by coating a photosensitive material onto a surface of the substrate.

However if particles, such as dust, contaminate the surface of the reticle, the photo-lithography process can be degraded, impairing the proper formation of circuit patterns on a substrate.

Under some circumstances, a pellicle is used to protect the circuit pattern formed on the reticle. The pellicle is a passivation layer that prevents contaminates such as dust from reaching the reticle. That is, the pellicle functions to protect a surface of reticle from air dust during a photo-lithography process. The pellicle is generally made of thin and transparent nitro-cellulose material.

However, when a pellicle is employed, particles can also adhere to the pellicle, thereby degrading the exposure process and impairing the proper formation of circuit patterning on a substrate.

In a conventional exposure device, a scanner using a light emitting diode (LED) laser is used to detect particles on the upper and lower side surfaces of a reticle, or a pellicle formed on the reticle.

FIG. 1 is a schematic view illustrating a detecting operation of a conventional particle detector.

As shown in FIG. 1, the conventional particle detector includes a light emitting device 50, a light receiving device 60, and a detecting member (not shown). Light emitting device 50 transmits light 40 to a reticle 10 or a pellicle 20, if applicable. Light receiving device 60 receives light 40 after it has been reflected by a surface of reticle 10 or pellicle 20. The detecting member analyzes light 40 and detects whether there are particles on the surface of reticle 10 or pellicle 20.

In detail, if light 40 emitted by light emitting device 50 is transmitted to a surface 22 of reticle 10 or pellicle 20 at a predetermined angle, and no particles are present, light 40 reflected by the same angle as the transmitted angle is received by light receiving device 60. However, when particles are present, light 40 transmitted by light emitting device 50 scatters, and only a portion of light 40 is received by light receiving device 60. Accordingly, the received light 40 is analyzed, and a determination is made as to whether particles are on present on reticle 10 or pellicle 20.

FIG. 2 is a schematic view illustrating a detecting operation of the conventional particle detector shown in of FIG. 1.

Particle detection is sometimes performed, even though pellicle 20 is not completely adhered to reticle 10, or a thickness of pellicle 20 is not uniform.

In the aforementioned cases, since an incident angle of light maintains a constant value based on the surface of pellicle 20 having a relative small thickness, only particles present at a surface of pellicle 20 are accurately detected. In contrast, it is difficult to accurately detect particles on a surface 12 of a reticle 10 without a pellicle, or on a surface 32 of a pellicle 30 having a relative larger thickness.

In the conventional particle detector, an incident angle of light should be changed as a function of the presence or the thickness of a pellicle. However, it is impossible for the conventional particle detector to adjust the incident angle of light. Therefore, particle detection accuracy varies significantly based on the type or the presence of the pellicle.

SUMMARY OF THE INVENTION

The present invention discloses a particle detector system including a light transmitting device adapted to transmit light beam to a target through an electrowetting microlens, a light receiving device adapted to receive the transmitted light beam reflected by a surface of the target, a light refraction angle adjusting controller adapted to apply a voltage to the electrowetting microlens in order to adjust an incident angle of the light irradiated, and a detector adapted to analyze the light received by the light receiving device to determine whether there are particles on a surface of the target.

The present invention also includes a method of detecting particles on a target by transmitting light beam to a target through an electrowetting microlens, receiving light beam reflected by a surface of the target, adjusting an incident angle of the transmitted light beam based on a type or presence of a pellicle of the target, and analyzing the received light to determine whether there are particles on the surface of the target.

BRIEF DESCRIPTION OF THE DRAWINGS

The above and other aspects of the present invention will become more apparent to those of ordinary skill in the art by the description of the preferred embodiments with reference to the attached drawings in which.

DETAILED DESCRIPTION OF THE INVENTION

Figure 1:
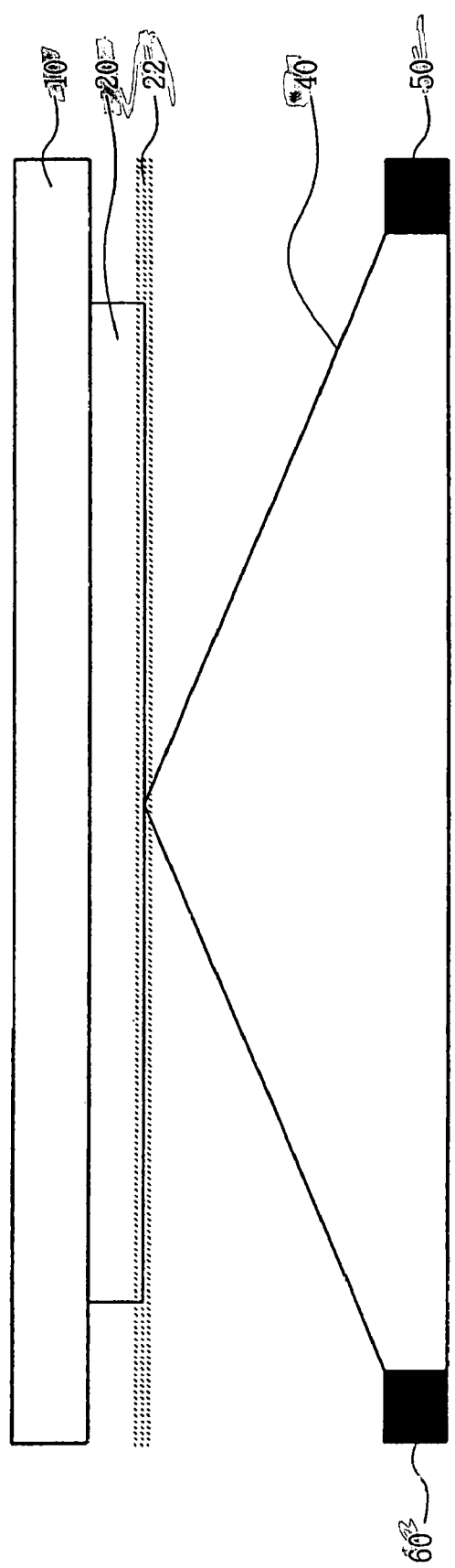
FIG. 1 is a schematic view illustrating a detecting operation of a conventional particle detector.
Figure 2:
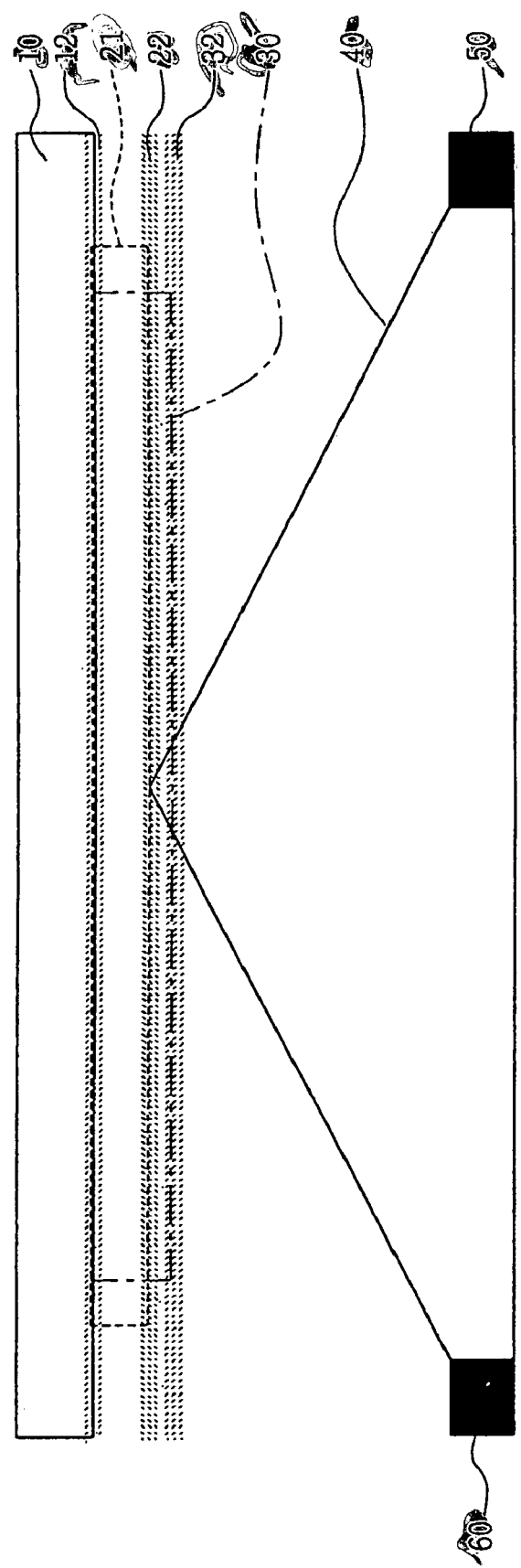
FIG. 2 is a schematic view illustrating a detecting operation of the conventional particle detector.
Figure 3:
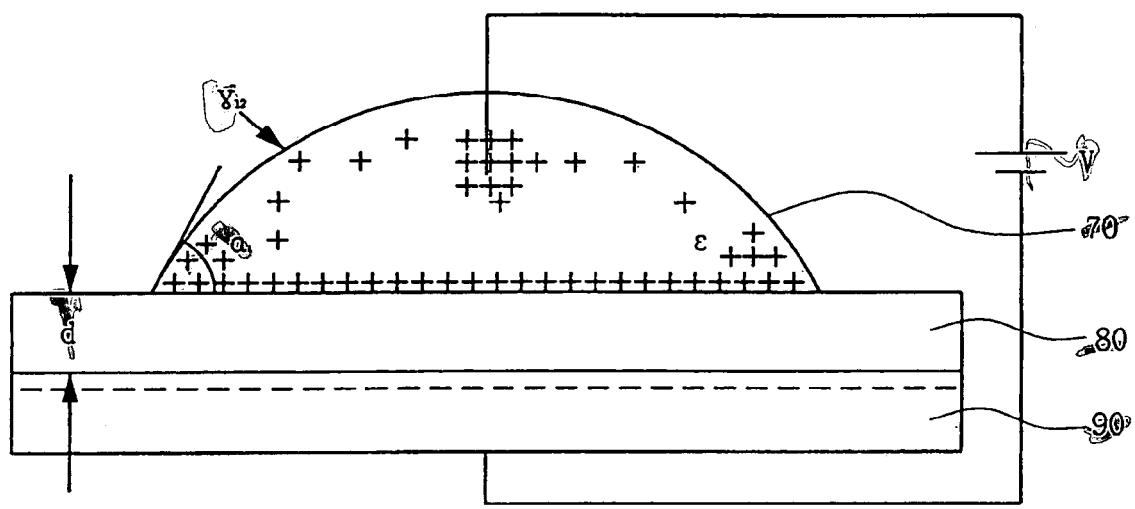
FIG. 3 is a schematic view illustrating an electrowetting phenomenon.

The present invention will now be described hereinafter with reference to the attached drawings, in which preferred embodiments of the present invention are shown. The present invention may, however, be embodied in different forms and should not be construed as limited to the embodiments set forth herein. Rather, these embodiments are provided as teaching examples of the present invention. Like numbers refer to like elements. The present invention embodies a particle detector using a liquid microlens. FIG. 3 shows a droplet 70 disposed on a dielectric insulating layer 80. Droplet 70 is preferably a conducting liquid such as water. An electrode 90 is positioned below dielectric insulating layer 80. When a voltage is applied between droplet 70 and electrode 90, droplet 70 spreads evenly across dielectric insulating layer 80.

This is referred to as an electrowetting phenomenon or electrocapillarity By the electrowetting phenomenon, contact angle a of droplet 70 is a function of the applied voltage V. The contact angle α(v) at any applied voltage, v, is determined by the Lippmann-Young's equation.

$$\cos\alpha(V) = \cos\alpha(O) + \frac{\varepsilon_0\varepsilon}{2\gamma_{12}d}V^2 \quad (1)$$

where, $\varepsilon_0\varepsilon$ is a dielectric constant of a dielectric insulating material, d is a thickness of the dielectric insulating material, $\gamma_{12}$ is an interfacial tension of a liquid-droplet interface, V is the applied voltage, and α(0) is the contact angle when the applied voltage is zero.

The electrowetting phenomenon has advantages in that it can be used to quickly, effectively, and reversibly control the shape of liquid. In a recently developed micro electromechanical system (MEMS), the electrowetting phenomenon can be created at a lower voltage of several volts.

U.S. Pat. No. 6,545,815, for example, discloses a liquid microlens electrowetting device.

Figure 4:
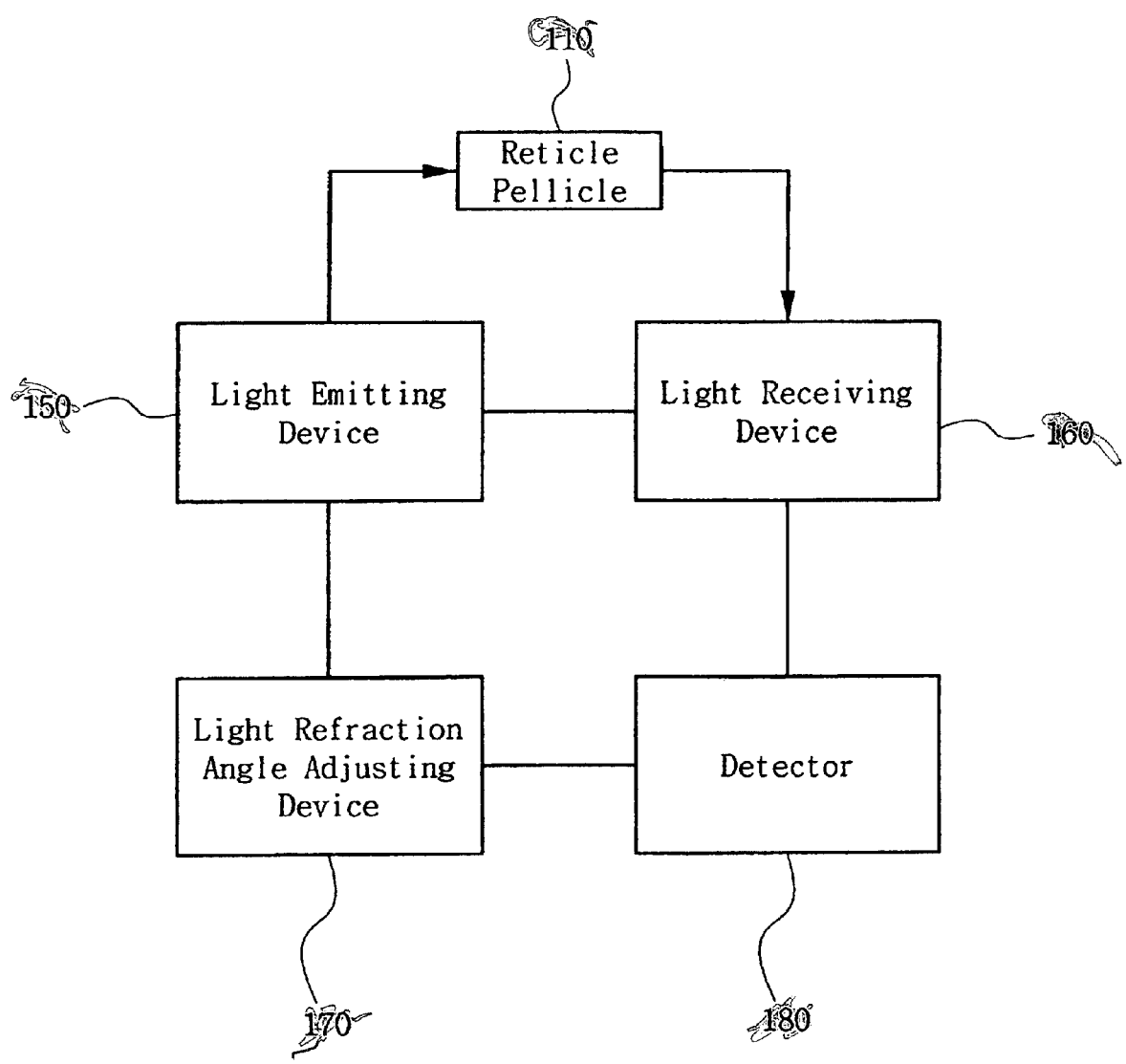
FIG. 4 is a block diagram illustrating a particle detector according to an embodiment of the present invention.

FIG. 4 is a block diagram illustrating a particle detector using an electrowetting microlens according to an embodiment of the present invention.

A particle detector for detecting particles on a reticle 110 (or a pellicle formed on reticle 110), according to an embodiment of the present invention includes a light emitting device 150, a light receiving device 160, a light refraction angle adjusting device 170, and a detector 180.

Light emitting device 150 includes a plurality of light beams sources (not shown) to generate the plurality of light beams, and an electrowetting microlens to refract and transmit the light beams by a predetermined angle based on an applied voltage. The light beams are preferably laser beams. Light emitting device 150 transmits light beams to a surface of a particle detecting target, such as reticle 110 or a pellicle.

At least one light beam is used as a reference light beam, and other light beams are used for real detection.

Light receiving device 160 receives the light transmitted by light emitting device 150 as reflected by reticle 110 or the pellicle. Light refraction angle adjusting device 170 adjusts an applied voltage to the electrowetting microlens in order to adjust an incident angle of the transmitted light. In response to a reference signal from detector 180, light refraction angle adjusting device 170 determines whether reticle 110 includes a pellicle, also determines a thickness of the pellicle, and adjusts the incident angle of the transmitted light based on these determinations.

Detector 180 analyzes the light received by the light receiving device 160, and detects whether there are contaminates (particles) based on the analyzed result.

Figure 5:
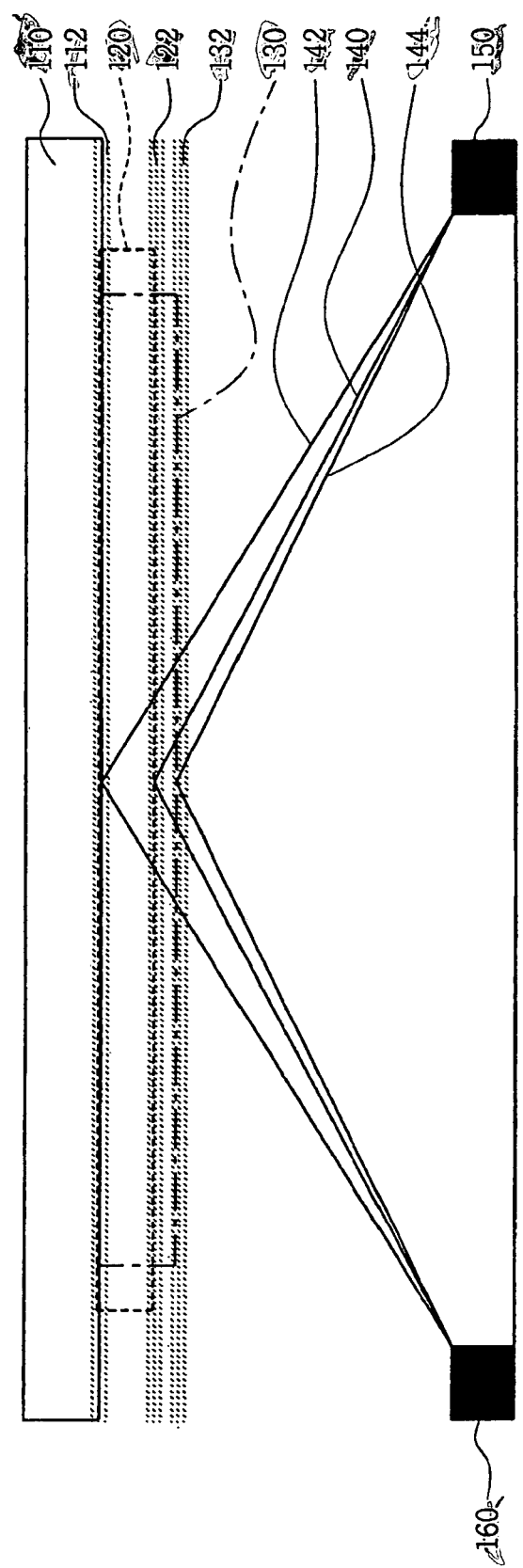
FIG. 5 is a schematic view illustrating a detecting operation of the particle detector.

FIG. 5 is a schematic view illustrating a detecting operation of the particle detector according to an embodiment of the present invention.

As illustrated in FIG. 5, a light emitting device 150 transmits light beams 140, 142, and 144. Respective refraction angles of light beams 140, 142, and 144 are determined by an electrowetting microlens. Light beams 140, 142, and 144 each having a determined refraction angle are transmitted to a reticle 110, pellicles 120, or 130. Namely, light beams 140, 142, and 144 are transmitted by a predetermined angle to be incident to a surface 112 of reticle 110 or surfaces 122 and 132 of pellicles 120 and 130, respectively.

A light refraction angle adjusting device 170 adjusts respective incident angles of light beams 140, 142, and 144. Light refraction angle adjusting device 170 sets a standard thickness, i.e., height, of pellicle 120 based on a reference light. The reference light is one of light beams 140, 142, and 144. To accurately detect particles that are present at surface 132, light refraction angle adjusting device 170 adjusts a voltage applied to an electrowetting microlens of a light emitting section 150 in order to adjust respective incident angles of light beams 140, 142, and 144.

Accordingly, if there are no particles on surfaces 112, 122, and 132, light receiving device 160 receives lights reflected by the same angle as the transmitted angle. In contrast to this, if particles are present on surfaces 112, 122, and 132, light beams 140, 142, and 144 are scattered at sections of surfaces 112, 122, and 132. In other words, only a portion of the light beams 140, 142, and 144 are received by light receiving device 160.

Detector 180 analyzes the laser beams received by light receiving device 160, and determines whether or not the particles are present based on the analyzed result.

As a result, particles can accurately be detected regardless of thickness, type, or the presence of a pellicle.

The present invention has been described using preferred exemplary embodiments. However, it is to be understood that the scope of the present invention is not limited to the disclosed embodiments. On the contrary, the scope of the present invention is intended to include various modifications and alternative arrangements within the capabilities of a person skilled in the art using presently known or future technologies and equivalents.

What is claimed is:

1. A particle detector system, comprising:
  a light transmitting device adapted to transmit a light beam to a target through an electrowetting microlens;
  a light receiving device adapted to receive the transmitted light beam reflected by a surface of the target;
  a light refraction angle adjusting device adapted to apply a voltage to the electrowetting microlens in order to adjust an incident angle of the transmitted light beam; and a detector adapted to analyze the light received by the light receiving device to determine whether there are particles on a surface of the surface of the target.

2. The system of claim 1, wherein the light transmitting device includes a laser.

3. The system of claim 1, wherein the light transmitting device includes a plurality of laser beams.

4. The system of claim 3, wherein one of the plurality of laser beams is a reference signal.

5. A method of detecting particles on a target, comprising:
transmitting light beam to a target through an electrowetting microlens;
receiving light beam reflected by a surface of the target;
adjusting an incident angle of the transmitted light beam based on a type or presence of a pellicle of the target; and
analyzing the received light to determine whether there are particles on the surface of the target and generating an output signal indicative of the determination.

6. The method of claim 5, wherein the incident angle of the transmitted light beam is adjusted by a refraction angle of the light beam as it passed through the electrowetting microlens.

7. The method of claim 6, wherein the refraction angle of the light beam as it passes through the electrowetting microlens is adjusted by applying a voltage the electrowetting microlens.

8. The method of claim 6, wherein the incident angle is adjusted based on a feedback signal.

9. The method of claim 5, wherein the light beam is transmitted by a plurality of lasers.

10. The method of claim 9, wherein one of the plurality of lasers is used as a reference signal.

11. The method of claim 5, wherein the light beam is transmitted by a light transmitting device, the reflected light beam is received by a light receiving device, and further comprising sending a reference signal from the light transmitting device to the light receiving device.

12. The method of claim 5, wherein the target is a reticle.

13. The method of claim 5, wherein the target is a pellicle.

* * * * *